(12) United States Patent
Zhang et al.

(10) Patent No.: US 7,643,876 B2
(45) Date of Patent: Jan. 5, 2010

(54) SYSTEM AND METHOD TO REDUCE DEVICE THERAPY PAIN

(75) Inventors: Yunlong Zhang, Mounds View, MN (US); Mark Schwartz, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 490 days.

(21) Appl. No.: 11/469,110

(22) Filed: Aug. 31, 2006

(65) Prior Publication Data

US 2008/0058877 A1    Mar. 6, 2008

(51) Int. Cl.
*A61N 1/39* (2006.01)
(52) U.S. Cl. .................. 607/5; 607/46; 607/63
(58) Field of Classification Search ............ 607/63
See application file for complete search history.

(56) References Cited

U.S. PATENT DOCUMENTS

| | | | |
|---|---|---|---|
| 4,343,301 A | 8/1982 | Indech | |
| 4,607,639 A | 8/1986 | Tanagho et al. | |
| 4,703,755 A | 11/1987 | Tanagho et al. | |
| 4,739,764 A | 4/1988 | Lue et al. | |
| 4,771,779 A | 9/1988 | Tanagho et al. | |
| 4,989,605 A | 2/1991 | Rossen | |
| 5,052,391 A | 10/1991 | Silberstone et al. | |
| 5,063,929 A | 11/1991 | Bartelt et al. | |
| 5,147,294 A | 9/1992 | Smith et al. | |
| 5,330,515 A | 7/1994 | Rutecki et al. | |
| 5,350,414 A | 9/1994 | Kolen | |
| 5,411,547 A | 5/1995 | Causey, III | |
| 5,562,718 A | 10/1996 | Palermo | |
| 5,792,187 A | 8/1998 | Adams | |
| 5,817,131 A | 10/1998 | Elsberry et al. | |
| 6,023,642 A | 2/2000 | Shealy et al. | |
| 6,044,303 A | 3/2000 | Agarwala et al. | |
| 6,091,989 A | 7/2000 | Swerdlow et al. | |
| 6,351,674 B2 | 2/2002 | Silverstone | |
| 6,393,323 B1 | 5/2002 | Sawan et al. | |
| 6,438,418 B1 | 8/2002 | Swerdlow et al. | |
| 6,701,185 B2 | 3/2004 | Burnett et al. | |
| 6,941,171 B2 | 9/2005 | Mann et al. | |
| 6,990,376 B2 | 1/2006 | Tanagho et al. | |
| 7,130,686 B1* | 10/2006 | Levine et al. | ............. 607/15 |
| 7,142,927 B2* | 11/2006 | Benser et al. | ............. 607/63 |
| 7,522,958 B2* | 4/2009 | Ideker et al. | ............. 607/5 |
| 2004/0088015 A1 | 5/2004 | Casavant et al. | |

FOREIGN PATENT DOCUMENTS

WO    WO 2008/027630 A1    3/2008

OTHER PUBLICATIONS

"PCT Application No. PCT/US2007/069007, International Search Report mailed Dec. 17, 2007", 5 pgs.
"PCT Application No. PCT/US2007/069007, Written Opinion mailed Dec. 17, 2007", 8 pgs.

* cited by examiner

*Primary Examiner*—Kennedy J Schaetzle
(74) *Attorney, Agent, or Firm*—Schwegman, Lundberg & Woessner, P.A.

(57) ABSTRACT

Systems and methods include sensing whether a shock to a heart is needed, and prior to delivering the shock, causing at least a partial contraction of a musculature in a chest, and delivering the shock while the musculature is at least partially contracted to reduce the pain of shock therapy.

32 Claims, 5 Drawing Sheets

SYSTEM AND METHOD TO REDUCE DEVICE THERAPY PAIN

FIELD

This application relates generally to medical devices and, more particularly, to systems, devices and methods for reducing device therapy pain.

BACKGROUND

Medical devices can be implanted to deliver electrical therapy to portions of the body to help alleviate certain medical conditions. Some medical conditions that may benefit from electrical therapy may include atrial tachyarrhythmia and/or ventricular tachyarrhythmia. For example, implantable electrodes can be coupled to a pulse generator. The electrode can be implanted in or near the heart and electrical therapy such as cardioversion or defibrillation shocks can be delivered from the pulse generator to the heart via the electrode.

However, these shocks can cause physiological stress, anxiety, and pain to the patient. The anticipation of the shock can cause anxiety and distress. As well, the shock itself can be painful. There is a need to reduce the pain of the device therapy.

SUMMARY

One aspect includes sensing whether a shock to a heart is needed, and prior to delivering the shock, causing at least a partial contraction of a musculature in a chest, and delivering the shock while the musculature is at least partially contracted.

One aspect includes sensing whether a therapeutic shock to a heart is needed, and before delivering the therapeutic shock, applying subcutaneous electrical neural stimulation near a pectoris major muscle.

DETAILED DESCRIPTION

The following detailed description and accompanying drawings show specific embodiments in which the present invention may be practiced. These embodiments are described in sufficient detail to enable those skilled in the art to practice the invention. Aspects of these embodiments can be combined and other embodiments may be utilized and structural changes may be made without departing from the scope of the present invention.

Figure 1:
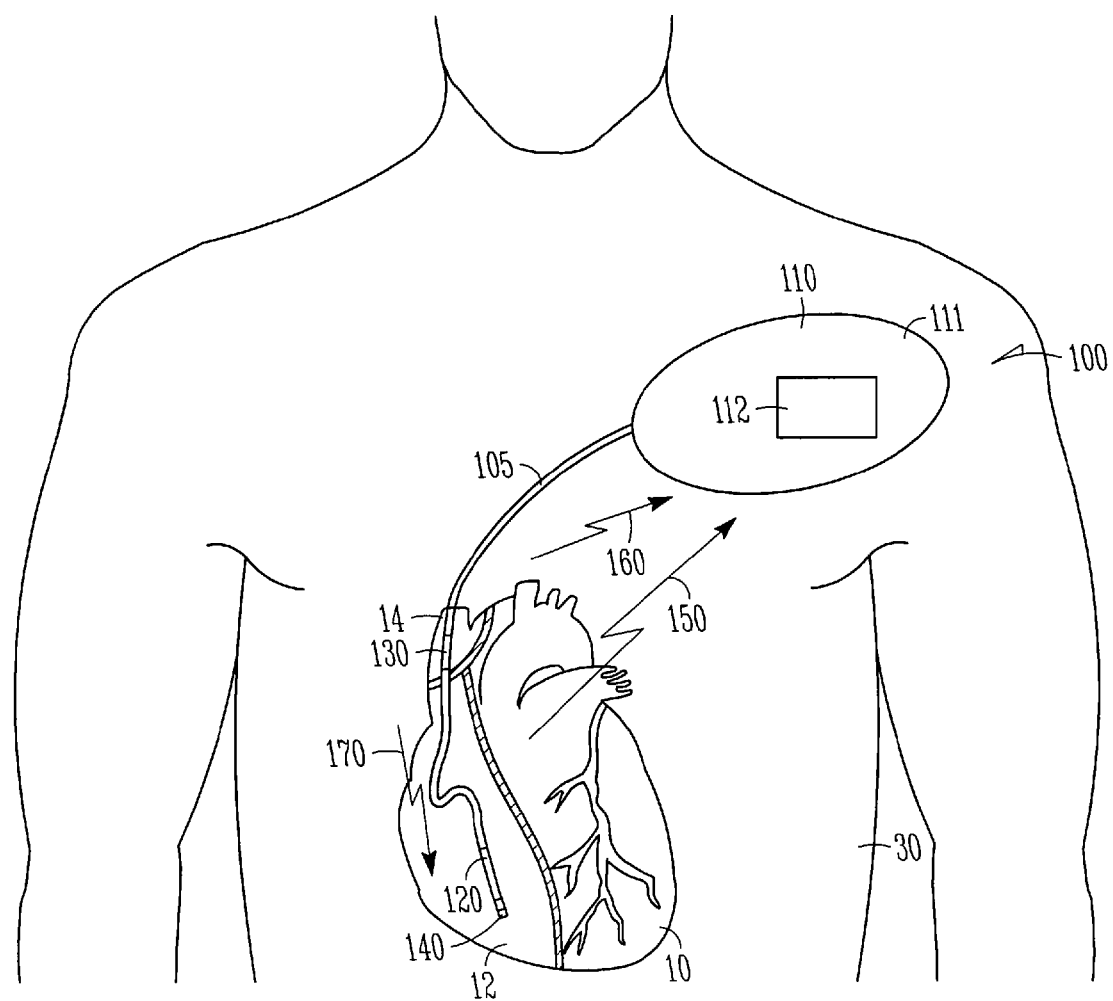
FIG. 1 shows a system to reduce device therapy pain, in accordance with certain embodiments.

FIG. 1 shows a system 100 for reducing pain during device therapy. System 100 generally includes a pulse generator 110 with at least one electrode 120 operatively coupled to the pulse generator. For example, electrode 120 can be a defibrillation or cardioversion electrode to deliver defibrillation pulses to a heart 10. The electrode can be located in the ventricle 12 or the atrium 14. Other embodiments can include a second defibrillation electrode 130, and/or a third electrode 140, such as a sensing electrode. More than three electrodes can be used. Electrodes 120, 130, and 140 can be disposed along a lead 105 which is coupled to pulse generator 110.

Pulse generator 110 includes controller circuitry 112 to control the functions of the pulse generator. Controller circuitry 112 can include hardware, software, and/or combinations of hardware and software programmed to deliver therapy shocks to heart 10, via one or more of electrodes 120, 130, and 140, such as atrial or ventricle defibrillation shocks or cardioversion shocks. In certain embodiments, pulse generator housing 111 can act as an electrode also.

In certain embodiments, pulse generator 110 is further adapted to deliver one or more pre-therapy conditioning electrical pulse or pulses to stimulate the chest musculature to reduce the startle effect from the muscle contraction from the shock in turn reducing the pain and/or anxiety caused by the therapy shock discussed above.

In certain embodiments, pulse generator 110 delivers one or more pre-therapy conditioning electrical pulses which can be directed so as to cause a preconditioning of the chest musculature similar to a fused tetanus condition of a musculature in a chest 30. A fused tetanus condition is when the chest musculature is at least partially contracted. Accordingly, the one or more pre-therapy conditioning electrical pulses cause at least a partial contraction of the musculature of the chest. The one or more pre-therapy conditioning electrical pulse or pulses are applied in such a manner that the chest musculature is still in the at least partially contracted state when the therapy shock is delivered. In certain embodiments, the one or more pre-therapy conditioning electrical pulse or pulses are applied recurrently or continually at least until the shock therapy is delivered. In certain embodiments, the pre-therapy conditioning electrical pulse or pulses can be applied recurrently or continually from a time prior to the therapy shock and continue so that the pulses partially or completely overlap with the therapy shock. This chest muscle contraction results in lessened pain once the therapy shock is delivered since the chest is pre-contracted. Thus, the patient is less surprised by the therapy shock and the muscles are not contracted as much by the therapy shock itself.

The one or more pre-therapy conditioning electrical pulses can be directed in different fashions. In certain embodiments, pre-therapy conditioning electrical pulses 150 are directed directly at the musculature of the chest from electrode 120 to pulse generator housing 111. In certain embodiments, pre-therapy conditioning electrical pulses 160 are directed at the musculature of the chest from electrode 130 to pulse generator housing 111. In certain embodiments, pre-therapy conditioning electrical pulses 170 are directed at the musculature of the chest from electrode 130 to electrode 120. The electrical pulses can be directed at musculature on the right side of the chest, the left side of the chest, or both sides.

In some embodiments, separate pulse generators are used to deliver therapy shocks and to apply pre-therapy conditioning pulses.

Figure 2:
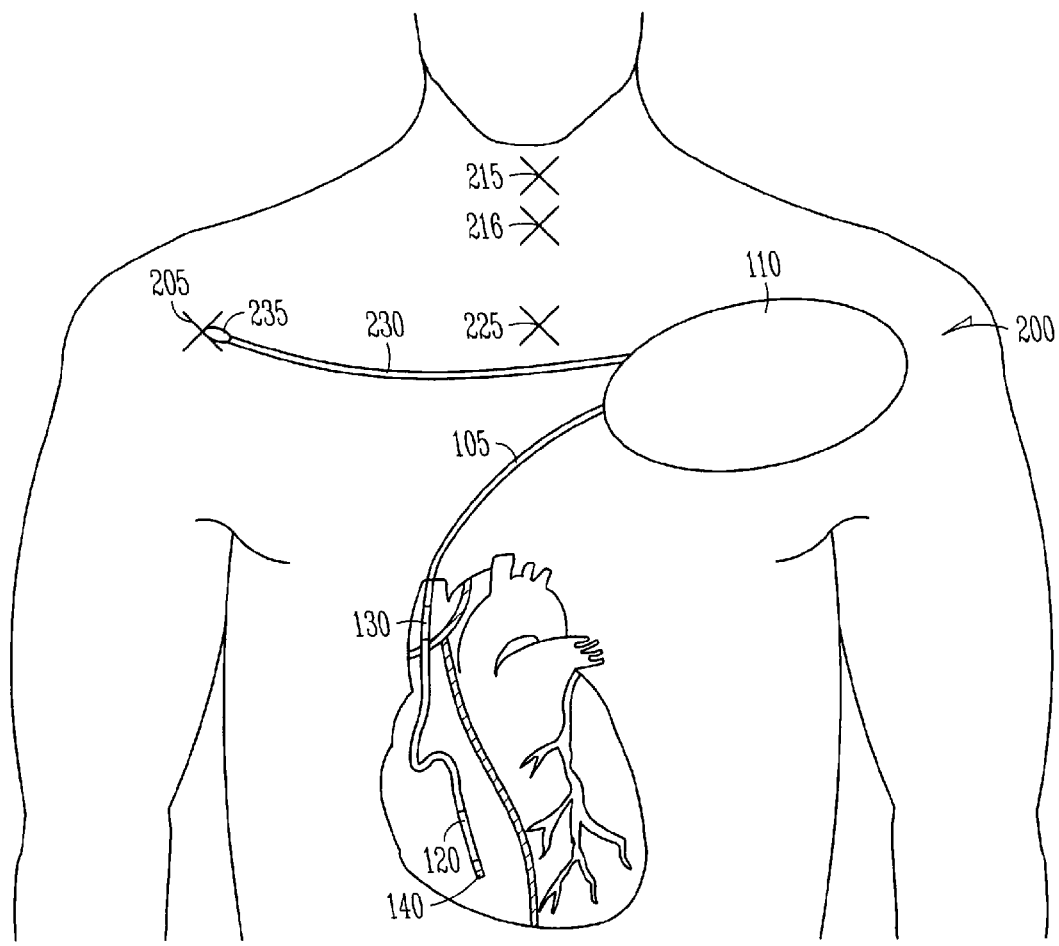
FIG. 2 shows a system to reduce device therapy pain, in accordance with certain embodiments.

FIG. 2 shows a system 200 to reduce device therapy pain, in accordance with certain embodiments. In this example, pulse generator 110 and electrode 120 can be implanted as discussed above. In this embodiment, an electrode 235 disposed along a second lead 230 is used to apply one or more pre-therapy conditioning electrical pulses. In this example, the pre-therapy conditioning electrical pulse or pulses are directed at one or more somatic nerves, such as anterior thoracic nerve 205. When a somatic nerve is signaled, the somatic nerve can cause the fused tetanus condition or chest muscle contraction, as discussed above. The somatic nerves control contraction of the chest muscles and by stimulating them at least up until the therapy shock is delivered, the patient's chest muscles are at least partially contracted and this lessens surprise and lessens the pain of contraction caused by the shock therapy itself.

Electrode 235 can be positioned to deliver therapy to a somatic nerve located anywhere in the body. In various embodiments, for example, electrode 235 can be implanted near or directed to deliver therapy to one or more somatic nerves in the back of the neck (the C7 upper subscapular nerve 215, or the C8 nerve 216, for example), the first thoracic spinal nerve T1 225 or the anterior thoracic nerve 205. Other embodiments can target other somatic nerve locations. Electrode 235 can include a tip electrode, a ring electrode, or a nerve cuff electrode, for example. In certain embodiments, an epidural nerve root stimulation lead can be used.

In some embodiments, separate pulse generators or electrodes are used to deliver therapy shocks and to apply pre-therapy conditioning pulses.

Figure 3:
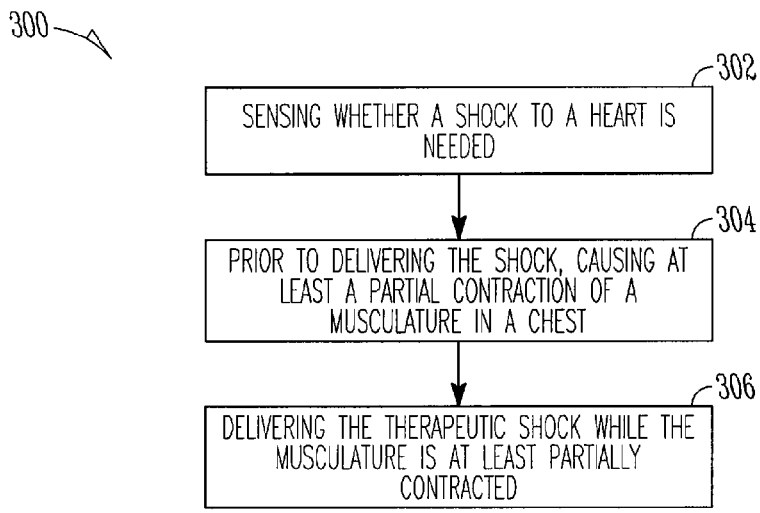
FIG. 3 shows a method to reduce device therapy pain, in accordance with certain embodiments.

FIG. 3 shows a method 300, in accordance with certain embodiments. Method 300 includes sensing whether a shock is needed (302), prior to delivering the shock, causing at least a partial contraction of a musculature in a chest (304); and delivering the therapeutic shock while the musculature is at least partially contracted (306).

In one example, as discussed above in FIG. 1, the pre-therapy conditioning pulses are directed at the musculature of the chest, and are at a level so as to cause at least a partially contracted condition in the chest muscles. In certain embodiments, as discussed above in FIG. 2, the pre-therapy conditioning electrical pulses include electrical pulses directed at somatic nerves such that the somatic nerves cause the fused tetanus condition. Some embodiments combine these two techniques. The somatic nerves can be stimulated in the back of the neck (the C7 upper subscapular nerve, or the C8 nerve, for example), the first thoracic spinal nerve (T1) or an anterior thoracic nerve.

The pre-therapy conditioning pulses directed at either the chest muscular, the somatic nerves, or both, are designed to at least partially contract the chest musculature in a fused tetanus condition. As discussed above, this pre-contraction of the chest muscles prepares the muscles for the therapy shock and helps reduce the startle reaction and/or the painful muscle contraction a patient feels when the therapy shock is delivered. The pre-therapy conditioning pulse or pulses are delivered at such a level and/or time that the chest muscles are still contracted when the therapy shock is delivered. Since the chest muscles are contracted right up until the shock therapy is delivered, the impact of the therapy shock on the musculature is reduced. In some examples, there can be up to about a 25 ms gap of time between the last of the one or more pre-therapy pulses and the beginning of the therapeutic shock since the muscle fibers will remain contracted.

In certain embodiments, sensing whether a shock is needed (302) includes sensing one or more electrical signals of a heart to determine if therapy is needed. For example, the pulse generator can include programming to recognize the need for atrial defibrillation or ventricle defibrillation, or any other shock therapy. When the pulse generator recognizes such a need, it then begins preparing to deliver the shock by charging a capacitor to deliver the shock therapy, which is typically between 1 J and 25 Joules, for example. The shock therapy can include cardioversion or defibrillation shocks for example.

In certain embodiments, the system can sense whether the therapy shock was successful. If the therapy was unsuccessful, then the system can repeat the procedure and provide the one or more pre-therapy condition pulses as many times as necessary.

In one embodiment, the pre-conditioning pulses of either embodiment discussed above can be in the about 20 to about 30 millisecond range, while the energy of the pulse will depend on the type of electrodes used. It is desired that the lowest energy be used to cause contraction. This can vary by person and electrodes used, since the voltage perception varies between patients (5V-50V, for example), and the pain perception varies as well (50V-200V, for example). Accordingly, in one embodiment, the device is programmable to deliver between about 5V to about 200V. In some embodiments, the pre-therapy conditioning can be programmed anywhere from about 10 Hz to about 100 Hz.

Figure 4:
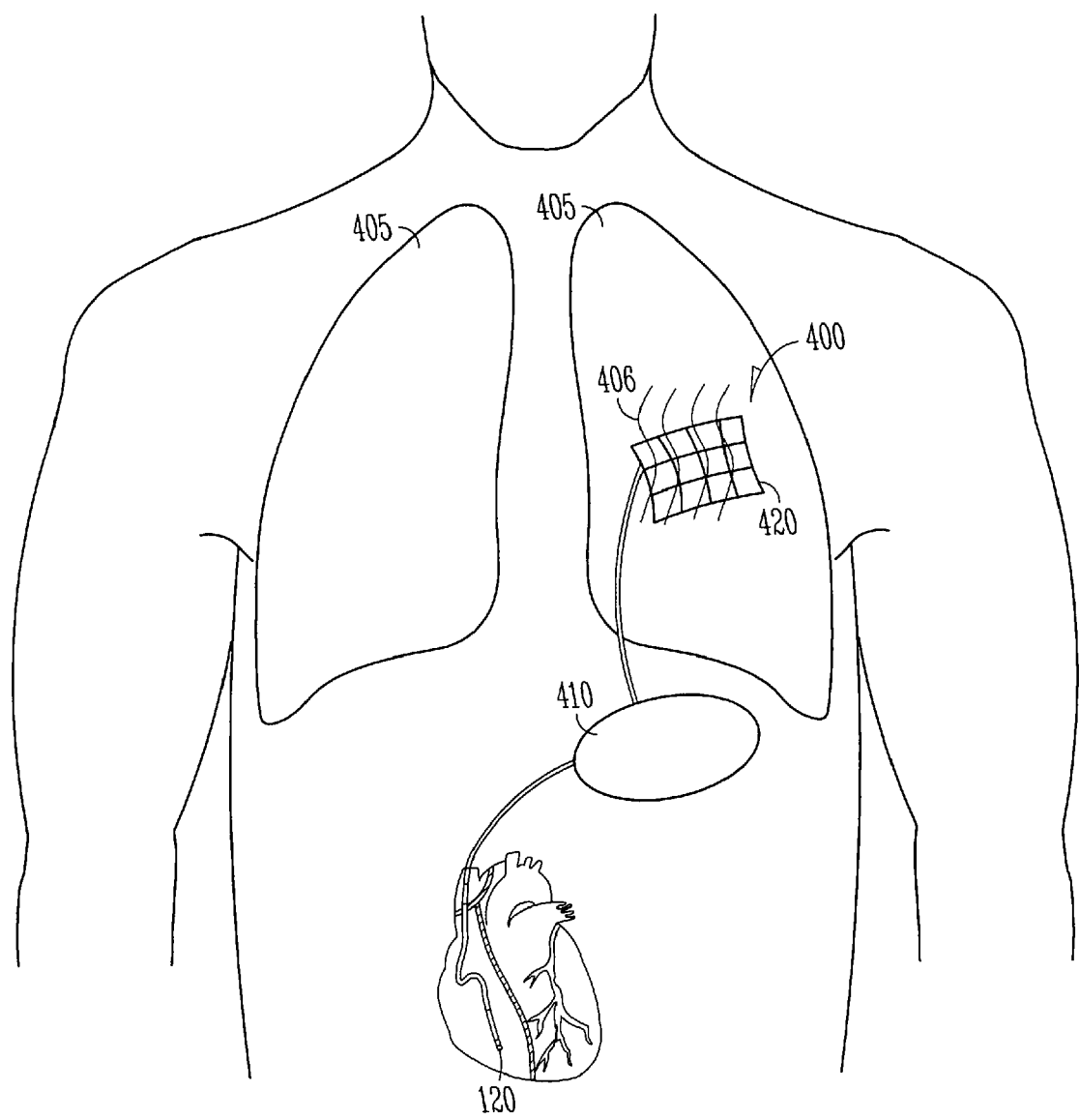
FIG. 4 shows a system to reduce device therapy pain, in accordance with certain embodiments.

FIG. 4 shows a system 400 to reduce device therapy pain, in accordance with certain embodiments. System 400 includes a pulse generator 410 and an electric mesh 420 adapted to deliver subcutaneous electrical neural stimulation prior to delivery of the shock therapy. An electrode 120 can further be couple to the pulse generator 410 to deliver the therapy shocks. In some embodiments, separate pulse generators or electrodes are used to deliver therapy shocks and to apply the subcutaneous electrical neural stimulation.

In certain embodiments, system 400 includes electrical mesh 420 implanted near or on the pectoris major muscles 405. In certain embodiments, applying subcutaneous electrical neural stimulation includes applying electrical pulses which stimulate pain nerve fibers 406 in the pectoris major muscles 405. In other embodiments, mesh 420 can be on the other side of the chest, or there can be an electrical mesh on both sides of the chest. By stimulating these nerve fibers, system 400 provides sedative therapy prior to and/or during and after the therapy shock. For example, the system can provide a pain signal conduction block, or can modulate pain signal transmission, and/or stimulate pain nerve fibers at a level so as to induce endogenous analgesics. This masks the pain and results in less pain from the subsequent therapy shock. This approach can help reduce pain, spasm and/or tetanus in the chest muscles.

Figure 5:
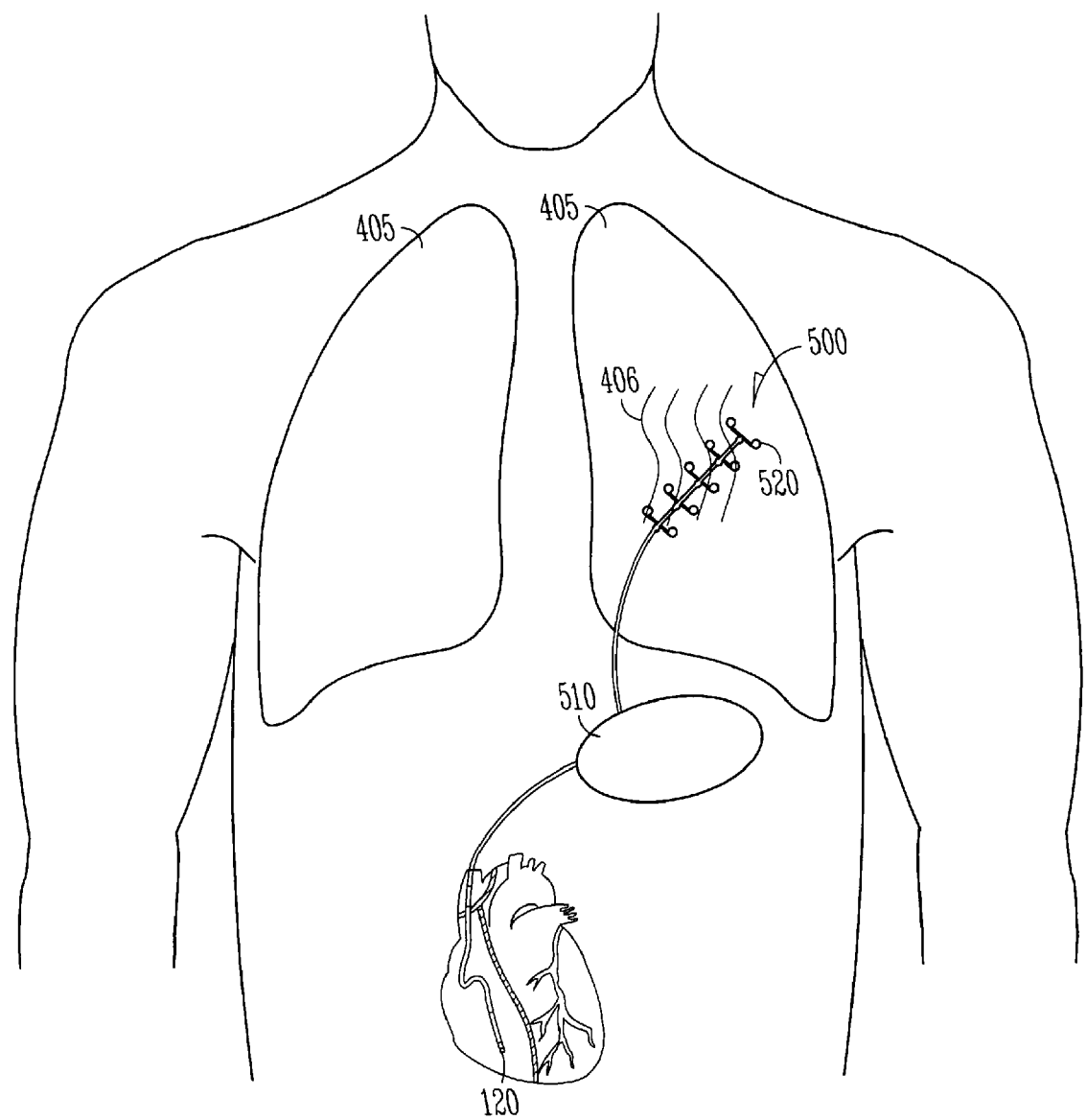
FIG. 5 shows a system to reduce device therapy pain, in accordance with certain embodiments.

FIG. 5 shows a system 500 to reduce device therapy pain, in accordance with certain embodiments. System 500 includes a pulse generator 510 and an electrode array 520 adapted to deliver subcutaneous electrical neural stimulation prior to delivery of the shock therapy. An electrode 120 can further be couple to the pulse generator 510 to deliver the therapy shocks, such as discussed above. In some embodiments, separate pulse generators or electrodes are used to deliver therapy shocks and to apply subcutaneous electrical neural stimulation.

In certain embodiments, system 500 includes electrode array 520 implanted near or on the pectoris major muscles 405. In certain embodiments, applying subcutaneous electrical neural stimulation includes applying electrical pulses which stimulate pain nerve fibers 406 in the pectoris major muscles 405. By stimulating these nerve fibers, the system provides a pain signal conduction block, modulates pain signal transmission, and/or stimulates pain nerve fibers at a level so as to induce endogenous analgesics. This results in less pain from the subsequent therapy shock.

Referring to both FIGS. 4 and 5, applying subcutaneous electrical neural stimulation can include the following stimulus parameters: an amplitude current at low intensity just above the threshold. A pulse width (duration) of about 10-1000 microseconds. A pulse rate (frequency) of about 40-150 impulses per second (Hz). One embodiment uses a frequency of about 80-100 Hz; or a pulse rate of about 0.5-10 Hz if the stimulus amplitude current is set at a high intensity. One embodiment uses a high stimulation frequency (about 40-150 Hz) and a low intensity, just above threshold, with the current set between about 10-30 mA. The pulse duration can be short (up to about 50 microseconds, for example). The onset of analgesia with this setup is almost immediate. Pain relief lasts while the stimulus is tuned on, and usually abates after the stimulation stops.

Figure 6:
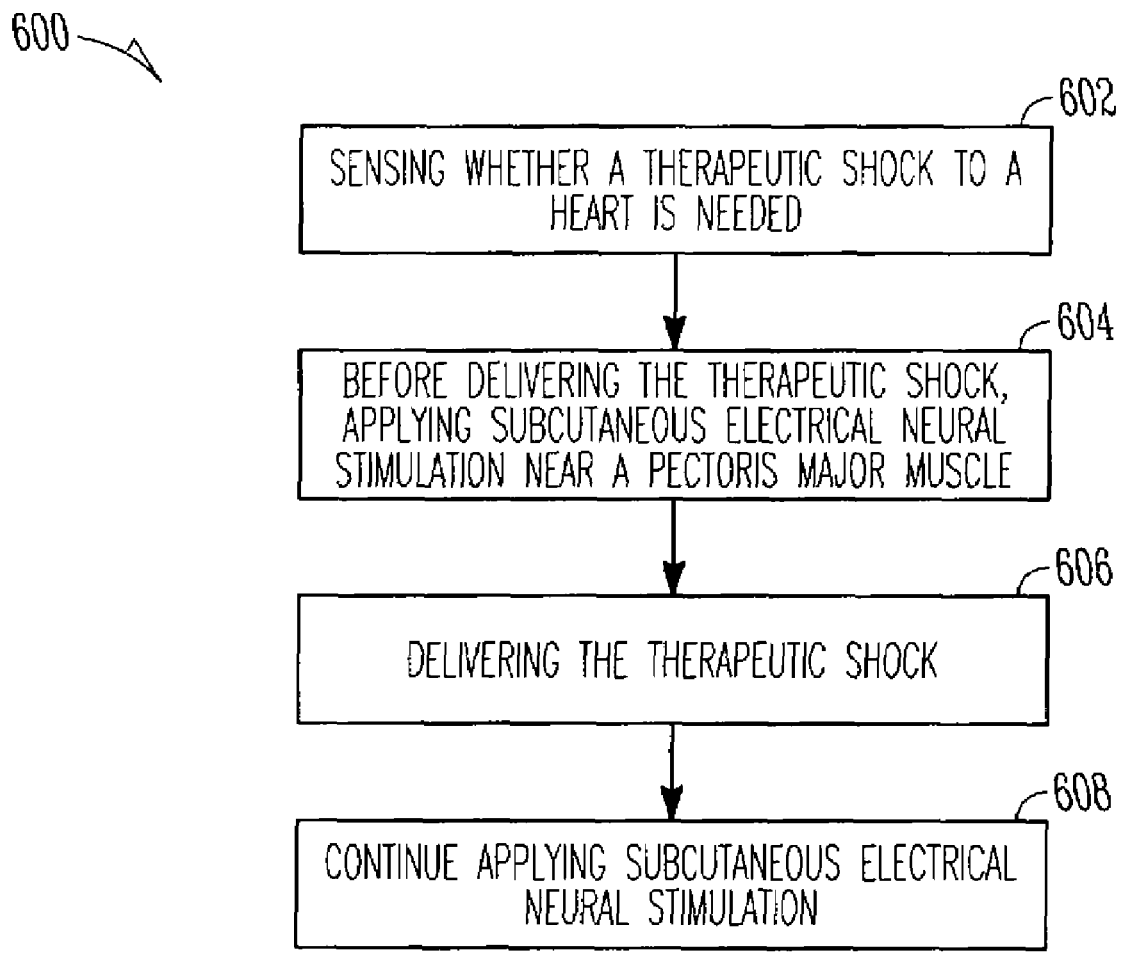
FIG. 6 shows a method to reduce device therapy pain, in accordance with certain embodiments.

FIG. 6 shows a method 600 to reduce therapy pain. Method 600 includes sensing whether a therapeutic shock is needed (602), before delivering the therapeutic shock, applying subcutaneous electrical neural stimulation (604), delivering the therapeutic shock (606), and continuing to deliver the subcutaneous electrical neural stimulation after the therapeutic shock (608). Certain embodiments omit continuing to deliver the subcutaneous electrical neural stimulation after the therapeutic shock.

As discussed above, sensing whether a therapeutic shock is needed includes sensing electrical signals of a heart. For example, the pulse generator can include programming to recognize the need for atrial or ventricle defibrillation. When the pulse generator recognizes such a need, it then begins preparing to deliver the shock by charging a capacitor to deliver the shock therapy, which is typically between 1 J and 25 Joules, for example. The shock therapy can include cardioversion or defibrillation shocks for example.

As discussed above, subcutaneous electrical neural stimulation can be applied via an electrical mesh implanted near the pectoris major muscles, or by an electrode array, for example. In certain embodiments, applying subcutaneous electrical neural stimulation includes applying electrical pulses which stimulate pain nerve fibers in the pectoris major muscles. By stimulating these nerve fibers, the method provides a pain signal conduction block, or modulates pain signal transmission, and/or stimulates pain nerve fibers at a level so as to induce endogenous analgesics.

In other embodiments, the pulse generator controller circuitry discussed above can be within the pulse generator or be a separate system communicating wirelessly with the pulse generator. In some embodiments, the pulse generator can include a transceiver and associated circuitry for use to communicate with a programmer or another external or internal device. Various embodiments can include wireless communication capabilities. For example, some transceiver embodiments use a telemetry coil to wirelessly communicate with a programmer or another external or internal device. Certain embodiments can utilize far-field ICDs.

The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method comprising:
sensing whether a shock to a heart is needed;
prior to delivering the shock, causing at least a partial contraction of a pectoris major muscle; and
delivering the shock while the muscle is at least partially contracted.

2. The method of claim 1, wherein causing at least a partial contraction of the pectoris major muscle includes applying one or more pre-therapy conditioning electrical pulses which are directed so as to cause the at least a partial contraction of the muscle.

3. The method of claim 2, wherein the one or more pre-therapy conditioning electrical pulses are applied at least until the shock is delivered.

4. The method of claim 2, wherein applying the one or more pre-therapy conditioning electrical pulses includes applying electrical pulses directed at the pectoris major muscle.

5. The method of claim 2, wherein applying the one or more pre-therapy conditioning electrical pulses includes applying electrical pulses directed at one or more somatic nerves such that a somatic nerve causes a fused tetanus condition.

6. The method of claim 2, wherein the one or more pre-therapy conditioning electrical pulses are delivered from within the heart.

7. The method of claim 1, wherein the shock includes a defibrillation shock.

8. The method of claim 1, wherein the shock includes a cardioversion shock.

9. The method of claim 1, wherein the one or more pre-therapy conditioning electrical pulses include pulses between about 5V to about 200V.

10. The method of claim 1, wherein the one or more pre-therapy conditioning electrical pulses include pulses between about 20 milliseconds to about 30 milliseconds.

11. A system comprising:
a pulse generator; and
at least one electrode operatively coupled to the pulse generator, wherein, in response to a need for shock therapy, the pulse generator is adapted to deliver one or more pre-therapy conditioning electrical pulses via the electrode so as to cause at least a partial contraction in a pectoris major muscle, and wherein the pulse generator applies the one or more pre-therapy conditioning electrical pulses from a time prior to delivery of the shock therapy at least until the shock therapy is delivered.

12. The system of claim 11, wherein the pulse generator also delivers the shock therapy.

13. The system of claim 11, wherein the one or more pre-therapy conditioning electrical pulses are directed at the pectoris major muscle.

14. The system of claim 11, wherein the pre-therapy conditioning electrical pulses are directed at one or more somatic nerves such that a somatic nerve causes a fused tetanus condition.

15. The system of claim 11, wherein the pulse generator is adapted to deliver the one or more pre-therapy conditioning electrical pulses recurrently until the shock therapy is applied.

16. The system of claim 11, wherein the shock therapy delivered by the system includes a defibrillation shock.

17. The system of claim 11, wherein the shock therapy delivered by the system includes a cardioversion shock.

18. The system of claim 11, wherein the one or more pre-therapy conditioning electrical pulses from the pulse generator include pulses between about 5V to about 200V.

19. The system of claim 11, wherein the one or more pre-therapy conditioning electrical pulses from the pulse generator include pulses between about 20 milliseconds to about 30 milliseconds.

20. A method comprising:
sensing whether a therapeutic shock to a heart is needed;

before delivering the therapeutic shock, applying subcutaneous electrical neural stimulation near a pectoris major muscle, wherein applying subcutaneous electrical neural stimulation includes applying electrical pulses at a level that stimulates pain nerve fibers; and delivering the therapeutic shock.

21. The method of claim 20, wherein the subcutaneous electrical neural stimulation is applied via an electrical mesh implanted near the pectoris major muscles.

22. The method of claim 20, wherein the subcutaneous electrical neural stimulation is applied via an electrode array implanted near the pectoris major muscles.

23. The method of claim 20, wherein applying subcutaneous electrical neural stimulation includes delivering electrical pulses at about 10 to 30 mA at a frequency of about 40 to 150 Hz which are delivered at least until the therapeutic shock is delivered.

24. The method of claim 20, wherein applying subcutaneous electrical neural stimulation includes applying one or more electrical pulses which stimulate pain nerve fibers at a level so as to provide a pain signal conduction block.

25. The method of claim 20, wherein applying subcutaneous electrical neural stimulation includes applying electrical pulses which stimulate a pain nerve fiber at a level so as to modulate pain signal transmission.

26. The method of claim 20, wherein applying subcutaneous electrical neural stimulation includes applying electrical pulses which stimulate a pain nerve fiber at a level so as to induce endogenous analgesics.

27. A method comprising:

sensing whether a therapeutic shock to a heart is needed; before delivering the therapeutic shock, applying subcutaneous electrical neural stimulation near a pectoris major muscle, wherein applying subcutaneous electrical neural stimulation includes delivering electrical pulses at about 10 to 30 mA at a frequency of about 40 to 150 Hz which are delivered at least until the therapeutic shock is delivered; and delivering the therapeutic shock.

28. A system comprising:

a pulse generator which, in response to a need for shock therapy, is adapted to apply subcutaneous electrical neural stimulation to a major pectoris muscle prior to delivery of the shock therapy, wherein the subcutaneous electrical neural stimulation includes the pulse generator applying electrical pulses at a level that stimulates pain nerve fibers.

29. The system of claim 28, wherein the subcutaneous electrical neural stimulation is applied via an electrical mesh.

30. The system of claim 28, wherein the subcutaneous electrical neural stimulation is applied via an electrode array.

31. The system of claim 28, wherein the pulse generator is also adapted to deliver the shock therapy.

32. A system comprising:

a pulse generator which, in response to a need for shock therapy, is adapted to apply subcutaneous electrical neural stimulation to a major pectoris muscle prior to delivery of the shock therapy, wherein applying subcutaneous electrical neural stimulation includes delivering electrical pulses at about 10 to 30 mA at a frequency of about 40 to 150 Hz.

* * * * *

UNITED STATES PATENT AND TRADEMARK OFFICE
CERTIFICATE OF CORRECTION

PATENT NO. : 7,643,876 B2  Page 1 of 1
APPLICATION NO. : 11/469110
DATED : January 5, 2010
INVENTOR(S) : Zhang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 617 days.

Signed and Sealed this

Twenty-first Day of December, 2010

David J. Kappos
*Director of the United States Patent and Trademark Office*